United States Patent [19]

Richardson, deceased et al.

[11] Patent Number: 4,666,967

[45] Date of Patent: May 19, 1987

[54] FLAME RETARDANTS FOR POLYURETHANES

[75] Inventors: Norman Richardson, deceased, late of Middleton, England, by Joyce Richardson, legal heir; Brian G. Clubley, Wilmslow; Richard J. Dellar, Hale, both of England

[73] Assignee: Ciba-Geigy Corporation, Ardsley, N.Y.

[21] Appl. No.: 821,178

[22] Filed: Jan. 22, 1986

[30] Foreign Application Priority Data

Jan. 23, 1985 [GB] United Kingdom ................ 8501704

[51] Int. Cl.$^4$ ........................... C07F 9/40; C07F 9/38; C08K 5/53; C08H 9/18
[52] U.S. Cl. ................ 524/130; 260/501.14; 260/501.17; 260/501.19; 260/502.52; 521/85; 521/107; 524/131; 524/132; 528/71; 528/72; 544/82; 544/85; 544/87; 544/106; 546/164; 546/189; 546/243; 546/244; 546/245; 558/131; 558/154
[58] Field of Search ................ 260/501.14, 501.17, 260/501.19, 502.5 E; 546/243, 244, 245, 189, 164; 524/130, 131, 132; 521/85, 107; 528/71, 72; 544/82, 85, 87, 106, 468, 491; 558/131, 154

[56] References Cited

U.S. PATENT DOCUMENTS

| | | | |
|---|---|---|---|
| 3,134,742 | 5/1964 | Wismer et al. | 521/107 |
| 3,400,085 | 9/1968 | Kujawa et al. | 524/130 |
| 3,963,437 | 6/1976 | Le Blanc et al. | 524/130 |
| 4,025,470 | 5/1977 | Andres et al. | 521/107 |
| 4,165,411 | 8/1979 | Marans et al. | |
| 4,308,197 | 12/1981 | Byrd et al. | |
| 4,341,694 | 7/1982 | Halpern | 521/85 |
| 4,403,075 | 9/1983 | Byrd et al. | |
| 4,407,981 | 10/1983 | Aaronson | 524/130 |
| 4,452,849 | 6/1984 | Nachbur et al. | |
| 4,487,800 | 12/1984 | Nachbur et al. | |

FOREIGN PATENT DOCUMENTS 919067 2/1963 United Kingdom .
999588 7/1965 United Kingdom .
1094717 12/1967 United Kingdom .

Primary Examiner—Veronica P. Hoke
Attorney, Agent, or Firm—Luther A. R. Hall

[57] ABSTRACT

The invention provides polyurethanes and polyisocyanurate having incorporated therein a flame retardant amount of a salt formed by reaction between dimethyl methyl phosphonate, monomethyl methyl phosphonate or methyl phosphonic acid, and a compound of the general formula (I).

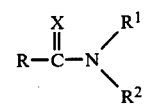

in which X is O, S or NH, $R^1$ is H, alkyl with 1 to 4 carbon atoms, alkenyl of up to 4 carbon atoms, CN, $CONH_2$ or $NH_2$, $R^2$ is H, alkyl with 1 to 4 carbon atoms or alkenyl of up to 4 carbon atoms or $R^1$ and $R^2$ together with the nitrogen atom to which they are attached form a heterocyclic ring of up to 6 carbon atoms which may optionally contain another hetero atom and R is H, an alkyl group with 1 to 8 carbon atoms, an aryl group with 6 to 10 carbon atoms, a cycloalkyl group with 5 to 12 carbon atoms or a heterocyclic group with up to 9 ring carbon atoms, or, together with $R^1$ forms an alkylene chain of 3 to 10 carbon atoms, or R is a group $NHR^3$ wherein $R^3$ is H, alkyl with 1 to 4 carbon atoms, alkenyl of up to 4 carbon atoms, CN, $CONH_2$ or $NH_2$ or together with $R^1$ forms an alkylene chain of 2 or 3 carbon atoms, or R is a group

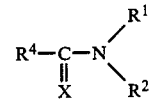

where $R^1$ and $R^2$ are as defined above and $R^4$ is a direct bond or an alkylene group having up to 8 carbon atoms or is an arylene group having 6 to 10 carbon atoms.

19 Claims, No Drawings

FLAME RETARDANTS FOR POLYURETHANES

The present invention relates to the use of organic salts of phosphonic acids in rendering polyurethanes and polyisocyanurates more flame retardant, and also to novel organic salts of phosphonic acids.

Polyurethanes and polyisocyanurates are usually made more flame retardant by adding a phosphorus-containing compound, a halogen-containing compound or a mixture thereof. One commonly used phosphorus-containing compound is dimethyl methyl phosphonate (DMMP)—see, for instance, British patent specifications Nos. 1094717, 999588 and 919067, and U.S. Pat. No. 4,165,411. However, there are certain problems associated with the use of DMMP. First it is a relatively volatile liquid (boiling point 181° C.) which means that material may be lost by volatilisation under certain circumstances. Secondly, DMMP is usually formulated with polyols used to manufacture polyurethanes and polyisocyanurates together with catalysts, blowing agents and other ingredients before the isocyanate is added. There is a tendency for the formulation to be somewhat unstable if it is stored for a long period before use. The viscosity of such formulations may increase on standing and variable forming characteristics may be observed when mixed with the isocyanate co-reactant.

Some salts of, inter alia, DMMP with amino compounds are known and are described in EP No. 0057668 and U.S. Pat. No. 4,308,197. However, the use of such salts as flame retardant additives for polyols or polyurethanes is not mentioned.

It is an object of the present invention to provide phosphorus-containing flame retardants of low volatility and which give polyol formulations which are stable on storage.

Accordingly the present invention provides a polyurethane or polyisocyanurate having incorporated therein a flame retardant amount of a salt formed by reaction between dimethyl methyl phosphonate, monomethyl methyl phosphonate or methyl phosphonic acid, and a compound of the general formula (I)

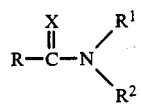

in which X is O, S or NH, $R^1$ is H, alkyl with 1 to 4 carbon atoms, alkenyl of up to 4 carbon atoms, CN, $CONH_2$ or $NH_2$, $R^2$ is H, alkyl with 1 to 4 carbon atoms or alkenyl of up to 4 carbon atoms or $R^1$ and $R^2$ together with the nitrogen atom to which they are attached form a heterocyclic ring of up to 6 carbon atoms which may optionally contain another hetero atom and R is H, an alkyl group with 1 to 8 carbon atoms, an aryl group with 6 to 10 carbon atoms, a cycloalkyl group with 5 to 12 carbon atoms or a heterocyclic group with up to 9 ring carbon atoms, or, together with $R^1$ forms an alkylene chain of 3 to 10 carbon atoms, or R is a group $NHR^3$ wherein $R^3$ is H, alkyl with 1 to 4 carbon atoms, alkenyl of up to 4 carbon atoms, CN, $CONH_2$ or $NH_2$ or together with $R^1$ forms an alkylene chain of 2 or 3 carbon atoms, or R is a group

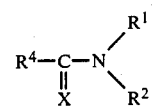

wherein $R^1$, $R^2$ and X are as defined above and $R^4$ is a direct bond or an alkylene group having up to 8 carbon atoms or is an arylene group having 6 to 10 carbon atoms.

Various compounds of formula (I) may be used. One suitable and preferred class of compounds has the general formula (II)

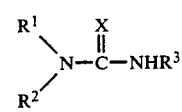

where $R^1$, $R^2$, $R^3$ and X are as defined above.

Another suitable class of compounds has the general formula (III)

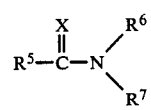

where $R^5$ is H, alkyl with 1 to 8 carbon atoms, an aryl, cycloalkyl or heterocyclic group; and $R^6$ and $R^7$ are the same or different and are H or an alkyl group with 1 to 4 carbon atoms, or $R^6$ and $R^7$ together with the nitrogen atom to which they are attached form a heterocyclic ring of up to 6 carbon atoms which may optionally contain another hetero atom, and X is as defined above.

Another suitable class of compounds has the general formula

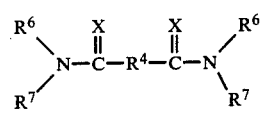

where $R^4$, $R^6$ and $R^7$ are as defined above.

Another suitable class of compounds has the general formula (V)

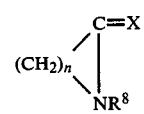

where $R^8$ is H or alkyl having 1 to 4 carbon atoms and n is an integer from 3 to 10, and X is as defined above.

When R or $R^5$ is a $C_1$-$C_8$ alkyl group it may be, for example, methyl, ethyl, isopropyl, n-butyl, sec-butyl, hexyl or octyl.

When $R^1$, $R^2$, $R^3$, $R^6$, $R^7$ or $R^8$ is a $C_1$-$C_4$ alkyl group it may be, for instance, methyl, ethyl, isopropyl, n-butyl or sec-butyl.

When $R^1$, $R^2$ or $R^3$ is alkenyl with up to 4 carbon atoms it may be, for instance, allyl, propenyl or butenyl.

When $R^1$ and $R^2$ or $R^6$ and $R^7$ form a heterocyclic ring, it may be, for instance, a pyridine, morpholine, piperidine, or piperazine ring.

When R is a heterocyclic ring with up to 9 carbon atoms it may be, for instance, a pyridine, morpholine, piperidine, indole or quinoline ring.

When R is an aryl ring with 6–10 carbon atoms it may be, for instance a benzene or naphthalene ring.

When R is a cycloalkyl ring with 5–12 carbon atoms it may be, for instance a cyclopentyl, cyclohexyl, cyclooctyl or cyclododecyl ring.

When $R^5$ is an aryl, cycloalkyl or heterocyclic group, it may be a radical such as those described above for R.

When R and $R^1$ together form an alkylene chain of 3 to 10 carbon atoms it may be, for isntance, propylene, butylene, hexylene or decamethylene.

When $R^4$ is an alkylene group having up to 8 carbon atoms it may be, for instance, methylene, ethylene, propylene, hexylene or octylene.

When $R^4$ is an arylene group having 6 to 10 carbon atoms it may be, for instance, phenylene or naphthylene.

The salts used in the present invention may be prepared by mixing dimethyl methyl phosphonate, monomethyl methyl phosphonate or methyl phosphonic acid with a compound of the general formula (I), defined above, optionally in an aqueous or organic solvent and optionally under an inert gas atmosphere, and heating if necessary to cause the salt to form.

The amount of dimethyl methyl phosphonate, monomethyl methyl phosphonate or methyl phosphonic acid is that which will react with one or more salt forming nitrogen atoms in the compound of formula (I) to give a mono-salt, di-salt or higher salt as desired. Usually a mono-salt or di-salt is prepared which will need one or two moles of phosphonic acid or ester per mole of compound of formula (I).

If methyl phosphonic acid or its monomethyl ester is used, formation of the salt is rapid and mild conditions may be used. The acid and compound of formula (I) may be simply mixed at room temperature to form the salt. If the compound of formula (I) is a viscous liquid or a solid, the mixture may be heated, e.g. up to 100° C. to ensure efficient reaction. If desired an aqueous or organic solvent may be used and is removed at the end of the reaction.

If DMMP is used, more vigorous reaction conditions are needed to ensure salt formation. The reaction mixture may be heated up to 180° C., optionally under an inert gas such as nitrogen. Heating at 100° C. to 180° C. for several hours may be needed. If desired the reaction may be performed in an aqueous or organic solvent, for example a hydrocarbon solvent such as toluene or xylene.

Methyl phosphonic acid and its esters and the compounds of formula (I) are all known compounds and can be prepared in various ways.

The salts used in the present invention are new compounds, with the exception of those formed from methyl phosphonic acid and dicyandiamide or methyl phosphonic acid and guanidine. These new compounds also form part of the present invention.

Examples of compounds of formula (I) which may be used to form salts include urea, dicyandiamide, guanidine, aminoguanidine, thiourea, N-methyl urea, N-allyl urea, N,N-diallyl urea, N,N'-dimethyl urea, ethylene urea, biuret, (thio) acetamide, (thio) propionamide, (thio) butyramide, (thio) octanamide, malonamide, mono- or di-thio malonamide, succinamide, mono- or di-thio succinamide, sebacamide, pyrrolidone, piperidinone, (thio) caprolactam and (thio) dodecalactam.

The salts used in the invention may be used alone or together with other flame retardants such as those given below for imparting flame retardance to rigid or flexible polyurethanes or polyisocyanurates. Polyurethanes and polyisocyanurates are prepared by reacting a polyol with a polyisocyanate, in the presence of a blowing agent if a foam is desired and a catalyst. The amount of polyisocyanate is varied to produce the desired product. The present invention is applicable to the whole range of polymers having an isocyanate index of from 1 to 6, preferably from 1 to 4.5.

The salts used in the invention may be incorporated into the polyurethane or polyisocyanurate by adding to the reaction mixture used to prepare the polyurethane or polyisocyanurate. Alternatively it may be added to the reactant containing hydroxyl groups (polyester or polyether polyol) prior to its reaction time the polyisocyanate. The viscosity of the polyol/salt mixture does not change appreciably on storage at room temperature and constant foaming conditions are achieved which do not vary with storage time.

The amount of flame retardant salt which may be incorporated in the polyurethane or polyisocyanurate depends on the level of flame retardancy required. Typically the amount of flame retardant salt may be from 1 to 100 parts, preferably 3 to 50 parts by weight per hundred parts by weight of polyol.

The salts may be mixed with other flame retardant compounds. These may be, for example, halogen-containing compounds such as aliphatic and aromatic bromine compounds, oxyalkylated phosphate esters, chloroalkyl phosphates, phosphonates or tri-aryl phosphates. Examples of suitable compounds are pentabromodiphenyl ether, dibromocresyl glycidyl ether, tetra-bromo bisphenol A, dibromoneopentyl glycol, a diol produced by the reaction of tetrabromomophthalic anhydride with ethylene oxide and/or propylene oxide, tris(chloroethyl)phosphate, tris(monochloropropyl) phosphate, diethyl bis(hydroxyethyl) aminomethyl phosphonate, and isopropylated or t-butylated phenyl phosphate mixtures as described in British Patent Specification No. 1146173, tricresyl phosphate, trixylyl phosphate and cresyl diphenyl phosphate.

The salts of the invention may also be used in admixture with amine salts of phosphonic acids of the general formula (VI) and/or (VII)

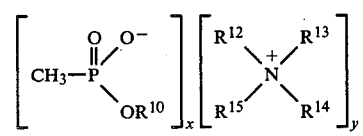

VI

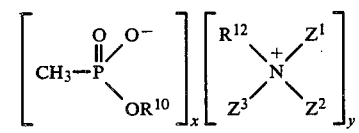

VII wherein
x and y are integers such that the number of negative and positive charges are the same, wherein $R^{10}$ and $R^{12}$ are hydrogen or methyl, $R^{13}$ is a $C_2$–$C_4$ alkyl group substituted by 1–3 hydroxyl groups, which may be substituted by an oxyalkylene chain, these being not more than one hydroxyl group on any one carbon atom, $R^{14}$ and $R^{15}$ may be the same or different and may be a group as defined for $R^{13}$, or hydrogen, a $C_1$-$C_4$ alkyl group, a phenyl group, a benzyl group, or a phenyl or benzyl group substituted on the aromatic ring by an alkyl group of 1-12 carbon atoms, a hydroxyl group, which may be substituted by an oxyalkylene chain, and/or 1-3 halogen atoms, or $R^{15}$ is a group of the formula (VIII)

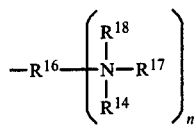

VIII wherein $R^{16}$ is an alkylene group of 2-4 carbon atoms, a phenylene group, a xylylene group, a diphenyl methane group or is a group of the formula

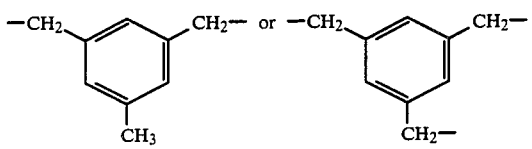

in which aromatic rings in a group $R^{16}$ may be substituted by an alkyl group of 1-12 carbon atoms, a hydroxyl group, which may be substituted by an oxyalkylene chain, and/or 1-3 halogen atoms, and $R^{17}$ is hydrogen or methyl, in which cases the nitrogen atom carries a positive charge, or $R^{17}$ is absent; $R^{18}$ is hydrogen or a group as defined for $R^{13}$ and n is 1 or 2;

or $R^{14}$ and $R^{15}$ may be joined to form, with the nitrogen, 5 or 6 membered heterocyclic ring, optionally containing an oxygen atom; and $Z^1$, $Z^2$ and $Z^3$ are the same or different and represent hydrogen, a $C_1$-$C_{12}$ straight or branched chain alkyl group, a $C_3$-$C_{12}$ straight or branched chain alkynyl group, a $C_4$-$C_{12}$ cycloalkyl group, a phenyl or naphthyl group which may be substituted by a $C_1$-$C_4$ straight or branched chain alkyl group, a $C_1$-$C_4$ alkoxy group, amino, methylamino, halogen or nitro, or a $C_7$-$C_{12}$ aralkyl group;

or $Z^2$ and $Z^3$ together with the nitrogen atom to which they are attached form a saturated or unsaturated 3-7 membered ring system which may optionally contain another hetero atom, and the ring system is optionally substituted by a $C_1$-$C_4$ straight or branched chain alkyl group, a $C_1$-$C_4$ alkoxy group, amino, methylamino, a $C_1$-$C_4$ aminoalkyl group, halogen or nitro;

or $Z^1$, $Z^2$ and $Z^3$ together with the nitrogen atom to which they are attached form an 8-12 membered bicyclic ring optionally containing another hetero atom, or $Z^1$ is a group of the formula

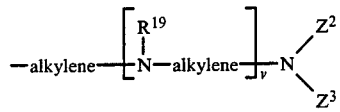

wherein alkylene is a group containing 2 to 12 carbon atoms, v is O or an integer from 1 to 5, $R^{19}$ is hydrogen or a $C_1$-$C_{16}$ straight or branched chain alkyl group, and $Z^2$ and $Z^3$ are as defined above;

or $Z^1$ is a group of the formula

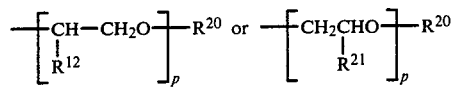

in which $R^{12}$ is as defined above, $R^{20}$ is a $C_1$-$C_{12}$ alkyl group and p is an integer from 1-10, preferably from 1-4;

or $Z^3$ is a group of the formula (VIIIa)

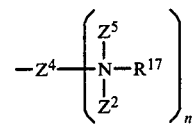

VIIIa wherein $Z^4$ is alkylene group of 2-12 carbon atoms, a phenylene group, a xylylene group, a diphenyl methane group or a group of the formula

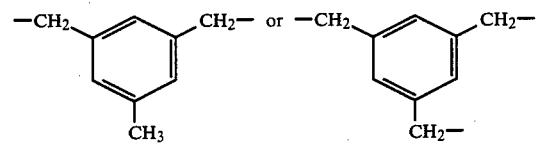

in which aromatic rings in a group $Z^4$ may be substituted by an alkyl group of 1-12 carbon atoms, hydroxyl and/or 1-3 halogen atoms, and $R^{17}$ is hydrogen or methyl, in which cases the nitrogen atom carries a positive charge, or $R^{17}$ is absent; $Z^5$ is hydrogen or a group as defined for $Z^1$ and n is 1 or 2; or $Z^2$ and $Z^5$ may be joined to form, with the nitrogen, a 3 to 7 membered heterocyclic ring, optionally containing another hetero atom.

The salts of formulae (VI) and (VII) may be prepared by mixing methyl phosphonic acid or ester of the formula

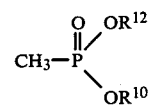

IX wherein $R^{12}$ is as defined above and $R^{10}$ is hydrogen or methyl, with an amine of the formula X and/or XI

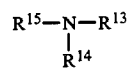

X

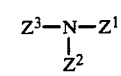

XI wherein $R^{13}$, $R^{14}$, $R^{15}$, $Z^1$, $Z^2$ and $Z^3$ are as defined above, optionally in aqueous or organic solvent and optionally under an inert gas atmosphere, and heating if necessary to cause the salt to form.

The amount of methyl phosphonic acid or ester of formula (IX) is that which will react with one or more of the amine groups in the amine of formula (X) or (XI) to give a mono-salt, di-salt or higher salt as desired.

The ratio of the salt to other flame retardant compounds may be from 5:95 to 95:5.

The compositions may also contain methyl phosphonic acid and its monomethyl or dimethyl esters which are not reacted with the compound of formula (I) present although, preferably, acidic additives are not present in the formulation.

The isocyanates and polyols used in making the polyurethane are polyisocyanurate can be any of those known in the art.

The isocyanate is ordinarily a liquid such as toluene di-isocyanate, methylene diphenyl di-isocyanate, polymeric methylene diphenyl di-isocyanate, hydrogenated methylene diphenyl di-isocyanate, hexamethylene di-isocyanate, isophorone di-isocyanate, and any polyisocyanate prepolymer containing two or more unreacted isocyanate radicals and the like. Conventionally, the toluene di-isocyanate used in the invention contains isomers of 2,4- and 2,6-toluene di-isocyanate. The concentration of these isomers is not critical.

The polyol for rigid foam may be a polyfunctional active hydrogen compound derived from the reaction of a polyhydroxylic compound such as glycerol, sucrose, sorbitol, trimethylol propane, pentaerythritol, triethanolamine, or an amine such as ethylenediamine, polyaromatic amine, or an aromatic Mannich base with propylene oxide and/or ethylene oxide.

Generally for production of flexible polyurethane foams the polyols are polyether polyols such as polyoxyethylene/oxypropylene diols, polyoxyethylene/oxypropylene triols, castor oil and methylglucoside polyether polyols having average molecular weights in the range of approximately 250–6500. Other polyols which may be used in place of polyether polyols are the polyester polyols, such as the reaction products of an aliphatic difunctional carboxylic acid, e.g. adipic acid, sebacic acid, with a di- or tri-functional hydroxy compound e.g. ethylene glycol, diethylene glycol, propylene glycol, 1,4-butylene glycol and butane triol.

Additionally polyols such as glycerol, hexane triol, butane triol, trimethylol propane, trimethylol ethane, and pentaerythritol, may be included in the polymerisation reaction with the polyol to maintain a desirable stoichiometrically balanced isocyanate to hydroxyl ratio.

In preparing the foamed polyurethanes and polyisocyanurates there can be used any of the conventional basic catalysts such, for example, as sodium hydroxide, sodium acetate, tertiary amines or materials which generate tertiary amines such as trimethylamine, triethylene diamine, N-methyl morpholine, N,N-dimethyl cyclohexylamine, and N,N-dimethyl aminoethanol. Also applicable are metal compounds such as hydrogen tin alkyl carboxylates, dibutyl tin diacetate, dibutyl tin dioctoate, dibutyl tin dilaurate and stannous octoate; as well as other compounds intended to promote trimersation of the isocyanate such as, 2,4,6-tris(N,N-dimethylamino methyl)phenol, 1,3,5-tris(N,N-dimethyl-3-aminopropyl)-s-hexahydrotriazine, potassium octoate, potassium acetate and catalysts such as those sold under the Trade Names DABCO®, TMR® and POLYCAT 43®.

Many other catalysts may be substituted for those listed above, as desired. The amount of catalyst used may be in the range of about 0.05% to about 5% or more by weight based upon the total weight of polyol(s) employed. Mixtures of the above and/or other catalysts may also be utilised.

To impart a foamed or cellular structure to the blended polyol-polyisocyanate mixture, a suitable blowing agent or system of blowing agents must be added or produced in-situ. Suitable blowing agents include the liquid but relatively volatile halogenated hydrocarbons such as dichlorodifluoromethane, trichlorofluromethane, and methylene chloride. These are added as liquids in quantities of about 5% to about 50%, by weight of the polyol, to the one or more components of the polyolpolyisocyanate mixture and are substantially volatilised in the liquid mixture to effect cell formation. Subsequently, the mixture cures to its final cellular shape.

Although the halogenated hydrocarbons are especially desirable as blowing agents when exceptional insulative properties are derived, other blowing agents, such as carbon dioxide generated by adding water to the polyol or simultaneously with the addition of the polyisocyanate, can be utilised especially for flexible open-celled foams.

It should also be noted that foaming may also be effected by combining the use of a blowing agent with the addition of water to the polyol.

In order to obtain relatively uniform distribution of the various components of the liquid system and to achieve the derived formation of bubbles, an emulsifier and/or surfactant may be incorporated into the mixture. These materials are physical in their effect and are not always necessary, especially if denser foams are desired. Any of the many hundreds of conventional surfactants can be used in amounts of up to 4% based on the weight of polyol used. Suitable surfactants are polydimethylsiloxane and polydimethylsiloxane polyalkylene copolymers, and the like known in the art.

It is also within the scope of the present invention to employ other materials in the compositions of the present invention where one desires to achieve a particular end result. Such materials include, without limitation, adhesion promotors, antioxidants, antistatic agents, antimicrobials, colourants, heat stabilisers, light stabilisers, pigments, plasticisers, preservatives, ultraviolet stabilisers, and fillers as described in Modern Plastics Encyclopedia, Volume 58, Number 10A, pages 170–187.

The invention is illustrated by the following Examples in which "parts" are parts by weight.

EXAMPLE 1

42.0 g (0.5 mole) dicyandiamide and 62 g (0.5 mole) dimethyl methyl phosphonate are heated to 140° C., under an atmosphere of nitrogen, and maintained at this temperature for 4 hours. The reaction mixture is cooled to 50° C. and the apparatus adapted for vacuum distillation. Unreacted dimethyl methyl phosphonate is removed at a pressure of 15.5 m/bar up to an internal temperature of 140° C.

There are obtained 74.5 g of an amber coloured resin. Analysis showed that the product is essentially

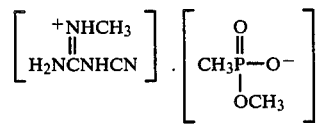

contaminated with about 16% unreacted dicyandiamide.

EXAMPLE 2

600 g (10 mole) urea and 1240 g (10 mole) dimethyl methyl phosphonate are heated for 14 hours at 140° C. under an atmosphere of nitrogen. The reaction mixture is cooled to 50° C. and the apparatus adapted for vacuum distillation. Unreacted starting materials are removed by distillation at a pressure of 15.6 m/bar up to an internal temperature of 140° C.

There are obtained 1645.8 g of a colourless viscous liquid amide salt, which has the following elemental analysis C, 25.90%; H, 7.13%; N, 15.47% and P, 16.62%. Calculated for $C_4H_{13}N_2O_4P$ C, 26.09%; H, 7.07%; N, 15.22% and P, 16.85%.

EXAMPLE 3

A solution of 96 g (1 mole) methylphosphonic acid in 100 mls water is added over 1 hour to a solution of 90 g (0.5 mole) guanidine carbonate in 100 mls water, at 25° C. During this time carbon dioxide is liberated from solution. The solution is stirred for a further 2 hours at 25° C. then evaporated to dryness. There are obtained 150.6 g of a colourless crystalline solid having analysis C, 15.03%; H, 6.73%; N, 27.05% and P, 19.79%. Calculated for $C_2H_{10}N_3O_3P$ C, 15.48%; H, 6.45%; N, 27.10% and P, 20.0%.

EXAMPLE 4

A solution of 96 g (1 mole) methylphosphonic acid in 100 g water is added over 1 hr. to a dispersion of 60 g (1 mole) urea in 60 g water. A clear solution is produced after 15 minutes. The solution is stirred a further half hour then evaporated to dryness. There are obtained 155 g of a colourless viscous liquid having analysis C, 15.43%; H, 5.65%; N, 17.89% and P, 19.91%. Calculated for $C_2H_9N_2O_4P$ C, 15.38%; H, 5.77%; N, 17.95% and P, 19.87%.

EXAMPLE 5

84 g (1 mole) dicyandiamide is added in portions, to a solution of 96 g (1 mole) methylphosphonic acid in 180 g water at 90° C., over 25 minutes. The solution is heated a further 45 minutes at 90° C. then evaporated to dryness. They are obtained 188.7 g of a colourless crystalline material which is purified by recrystallisation from 1.5 liters ethyl alcohol. 63.4 g of material melting at 163°–4° C. are obtained. The material has the following analysis C, 18.53%; H, 5.40%; N, 28.43% and P, 15.90%. This corresponds to $C_3H_{11}N_4O_4P$. The infrared spectra shows no peak corresponding to nitrile (—C≡N). During the preparation the nitrile group hydrolises to amide producing the compound

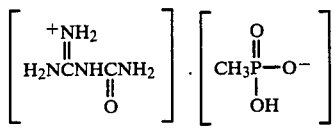

EXAMPLE 6

135 g (0.96 moles) N,N-diallylurea are heated at 100° C. under a nitrogen atmosphere whilst 119.6 g (0.96 moles) dimethylmethylphosphonate are added dropwise over 2 hours. The reaction mixture is heated for a further 5½ hours at 100° C. then cooled to ambient temperature. The apparatus is adapted for vacuum distillation and unreacted starting materials are removed by heating up to 100° C. under a pressure of 19.5 m bar. There are obtained 253 g of a pale yellow liquid, which has elemental analysis C, 45.03%; H, 8.24%; N, 10.37% and P, 11.96%. Calculated for $C_{10}H_{21}N_2O_4P$, C, 45.45%, H, 7.95%; N, 10.60% and P, 11.74%.

EXAMPLE 7

100 g (1 mole) allyl urea and 124 g (1 mole) dimethyl methyl phosphonate are mixed and heated at 140° C. under a nitrogen atmosphere for a total time of 22½ hours. The reaction mixture is cooled to 25° C. and the apparatus adapted for vacuum distillation. Unreacted starting materials are removed by heating to 140° C. at a pressure of 19.5 m bar of Mercury. There are obtained 193.1 g of pale yellow liquid having a phosphorus content of 13.88%. Calculated for $C_7H_{17}N_2O_4P$, P=13.84%.

EXAMPLE 8

74 g (1 mole) N-methyl urea and 124 g (1 mole) dimethyl methyl phosphonate are reacted at 140° C. under a nitrogen atmosphere for a total of 17½ hours. After removal of unreacted starting materials by vacuum stripping at a pressure of 15.6 m bar there are obtained 172.3 g of colourless liquid having a phosphorus content of 15.92%. Calculated for $C_5H_{15}N_2O_4P$, P=15.65%.

EXAMPLE 9

103 g (1 mole) N-(2-hydroxyethyl)acetamide are added over 2 hours to 124 g (1 mole) dimethyl methyl phosphonate at 140° C. The reaction mixture is heated for a further 21½ hrs. at 140° C. After removal of unreacted starting materials by vacuum stripping at a pressure of 19.5 m bar there are obtained 187 g of pale yellow liquid having a phosphorus content of 13.86%. Calculated for $C_7H_{18}NO_5P$, P=13.66%.

EXAMPLE 10

103 g (1 mole) biuret and 124 g dimethyl methyl phosphonate are heated at 140° C. under a nitrogen atmosphere for a total of 11½ hours. After removal of unreacted starting materials under vacuum at 19.5 m bar pressure there are obtained 186 g of a white coloured viscous liquid having a phosphorus content of 14.65%, calculated=13.66%, and containing 9.0% unreacted biuret.

EXAMPLE 11

59 g (1 mole) acetamide and 124 g (1 mole) dimethyl methyl phosphonate are heated, in a 4-necked flask fitted with stirrer, thermometer and fractionating column, at 140° C. for a total of 24 hours. The methyl acetate by product is separated in the fractionating column and collected in a receiver via a water-cooled condenser.

After cooling to 25° C. and standing for 24 hours there are isolated by filtration 22.8 g of pale yellow crystals. This crystalline material is purified by dissolving in methanol, treatment of the solution with activated carbon and evaporation of the solvent to give 19.1 g of white crystals having melting point 150°–1° C. These crystals have elemental analysis, C 27.90%, H 7.63%, N—16.80% and P 18.24%. $^1H$ and $^{13}C$ nmr shows that these crystals are

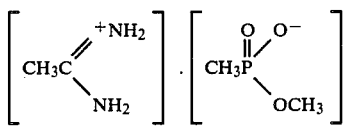

EXAMPLE 12

88 g (1 mole) N,N'-dimethyl urea and 124 g (1 mole) dimethyl methyl phosphonate are reacted at 140° C. under a nitrogen atmosphere for a total of 32 hours. After removal of unreacted starting materials up to a temperature of 140° C. at a pressure of 15.6 m bar there obtained 184.4 g of colourless liquid having a phosphorus content of 14.71%. Calculated for $C_{16}H_{17}N_2O_4P$, P=14.62%.

EXAMPLE 13

124 g (1.0 mole) dimethyl methyl phosphonate are heated to 140° C. 73 g (0.86 moles) pyrrolidone are added over 2 hours. The reaction mixture is heated a total of 48 hours at 140° C. Unreacted starting materials are removed by vacuum stripping at a pressure of 15.6 m bar. There are obtained 113.3 g of a dark coloured viscous fluid having a phosphorus content of 14.57%. Calculated for $C_7H_{16}NO_4P$, P=14.83%.

EXAMPLE 14 113 g (1 mole) caprolactam are melted under a nitrogen atmosphere by heating to 140° C. 124 g (1 mole) dimethyl methyl phosphonate are added over 2 hours after which time the reaction mixture is heated for a further 12 hours at 140° C. and 29 hours at 160° C. Unreacted dimethyl methyl phosphonate is removed by vacuum stripping at a pressure of 19.6 m bar. The dark brown viscous liquid obtained is dissolved in methanol and decolourised by treating with activated carbon. The pale yellow solution is evaporated to dryness and allowed to stand at ambient temperature for 14 days, during which time unreacted caprolactam crystallises from the product. The mixture is filtered to remove the crystalline caprolactam, there are obtained 154.9 g of a yellow viscous liquid, containing 15% by weight unreacted caprolactam, having phosphorus content 9.93%. Calculated for $C_9H_{20}NO_4P$, P=13.08%.

EXAMPLE 15

86 g (1 mole) 2-Imidazolidone and 124 g (1 mole) dimethyl methyl phosphonate are heated under a nitrogen atmosphere at 140° C. for 24 hours. The reaction mixture is cooled to 60° C. the apparatus adapted for vacuum distillation and unreacted starting materials removed at a pressure of 15.6 m bar. There are obtained 169 g of a pale brown viscous liquid having a phosphorus content of 14.62%. Calculated for $C_6H_{15}N_2O_4P$, P=14.76%.

EXAMPLE 16

90 g (2 moles) Formamide and 124 g (1 mole) dimethyl methyl phosphonate are heated in a 4-necked flask fitted with a stirrer, thermometer and fractionating column leading via a water cooled condenser to an ice cooled receiver, at 140° C. for a total of 18½ hours. The methyl formate by product is separated via the fractionating column.

After cooling to 60° C. unreacted starting materials are removed by vacuum stripping at 15.6 m bar up to a final temperature of 120° C. The dark coloured product is dissolved in 200 mls methanol and treated with activated carbon. After removal of the methanol there are obtained 142.5 g of a yellow coloured viscous liquid having phosphorus content=19.97%. Calculated for $C_3H_{11}N_2O_3P$, P=20.12%.

$^1H$, $^{31}P$ and $^{13}C$ nmr spectroscopy shows that the product is

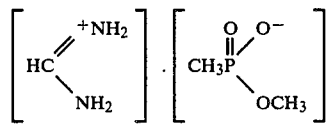

EXAMPLE 17

360 g (6 mole) urea are charged to a flask and heated to 150° C. At this temperature a solution of 744 g (6 mole) dimethyl methane phosphonate and 74.4 g (4.13 mole) water are added to the urea over a period of seven hours. The reaction mass is maintained at 150° C. for a further 1 hour before being cooled to 60° C. and run off. P nmr on the product shows that 97.8% of the DMMP has been reacted.

There are obtained 969.4 g of a colourless liquid with a viscosity of 31560 c/p at 25° C. Elemental analysis is similar to that in Example 2.

EXAMPLES 18-35

The following examples illustrate the ease with which flame retardant rigid foamed polyurethane compositions may be produced from polyols and polymeric diphenyl methane diisocyanate in accordance with the present invention.

The following foam formulation was utilised to show the effect of flame retardant

| Reactant | Concentration (parts by weight) |
|---|---|
| Thanol ® R650x[1] | 100 |
| Water | 0.2 |
| Silicone surfactant | 2 |
| Trichloro fluoro methane | 40 (to foam density 30 ± 1 kg./m³) |
| Flame retardant | 10 |
| Suprasec ® DND[2] | to index of 1.05 |

[1]Thanol ® is an aromatic polyol.
[2]Suprasec ® is a polymeric diphenyl methane diisocyanate.

The above ingredients were mixed together for 10 seconds in a high speed stirrer (2000 rpm) at room temperature, with the isocyanate being added last, and then poured immediately into a cardboard mould. The exothermic reaction which ensued was allowed to free rise the foam. The time until the foam is no longer tack is designated as the non-tack time. After attainment of the non-tack time, the foam is aged for 3 days at ambient temperature.

The specimens were cut from the foam and subjected to the limiting Oxygen Index Test and DIN 4102 B2 vertical Burn test. Results are shown in the Table below, as a comparison the same foam material has been produced without flame retardant. The foams obtained from Examples 18-35 exhibited no splits, no distortion, and no scorching.

| Example | Additive | Oxygen Index | DIN 4102 B2 Test | | | Foam parameters* | | |
|---|---|---|---|---|---|---|---|---|
| | | | Time to Spec. mark (sec) | Max. Flame Height (cm) | Burn Time (sec) | CT (sec) | RT (sec) | NTT (sec) |
| — | None | <21 | 3 | >20 | >60 | 17 | 70 | 120 |
| 18 | Product of Example 1 | 23.5 | 5 | 15 | 13 | 19 | 76 | 131 |
| 19 | Product of Example 2 | 25.1 | — | 13 | 13 | 16 | 36 | 64 |
| 20 | Product of Example 3 | 24.9 | 5 | 15 | 9 | 14 | 50 | 87 |
| 21 | Product of Example 4 | 25.6 | — | 14 | 12 | 6 | 32 | 71 |
| 22 | Product of Example 5 | 24.2 | — | 14 | 11 | 23 | 130 | 205 |
| 23 | Product of Example 6 | 23.7 | 5 | 15 | 10 | 10 | 24 | 32 |
| 24 | Product of Example 7 | 24.2 | 5 | 15 | 11 | 15 | 33 | 43 |
| 25 | Product of Example 8 | 25.1 | — | 13 | 10 | 11 | 27 | 37 |
| 26 | Product of Example 9 | 24.3 | 6 | 16 | 9 | 13 | 31 | 46 |
| 27 | Product of Example 10 | 22.4 | 4 | 16 | 14 | 23 | 120 | 150 |
| 28 | Product of Example 11 | 24.5 | — | 14 | 9 | 17 | 54 | 90 |
| 29 | Product of Example 12 | 24.3 | 5 | 16 | 10 | 13 | 31 | 46 |
| 30 | $H_2NC(SCH_3)=NH_2$ + $CH_3P(=O)(O^-)(OCH_3)$ | 24.4 | 5 | 15 | 15 | 20 | 110 | 147 |
| 31 | Mixture** | 25.4 | — | 12 | 11 | 11 | 25 | 39 |
| 32 | Product of Example 13 | 24.2 | 5 | 15 | 10 | 15 | 32 | 59 |
| 33 | Product of Example 14 | 23.8 | 6 | 16 | 13 | 15 | 37 | 64 |
| 34 | Product of Example 15 | 24.2 | 5 | 15 | 15 | 11 | 30 | 64 |
| 35 | Product of Example 16 | 25.5 | — | 14 | 11 | 6 | 19 | 57 |

*CT = cream time
RT = rise time
NTT = non-tact time

EXAMPLES 36-38

The formulation given for Examples 18-35 with the exclusion of trichlorofluoromethane and Suprasec ® DND is made up and kept at a temperature of 50° C. After 1 month and 2 months samples are removed, cooled to 23° C. and their viscosity (Brookfield) measured. A further 112.2 parts is diluted with 40 parts trichlorofluoromethane and then mixed with Suprasec DND to an index of 1.05 by the method given in Examples 18-35.

Results are shown in the table below:

| Example | Additive | Storage time at 50° C. | Viscosity % increase | Foam parameters | | | OI % |
|---|---|---|---|---|---|---|---|
| | | | | CT (sec) | RT (sec) | NTT (sec) | |
| 36 | Product of Example 2 | 0 | 0 | 16 | 36 | 64 | 25.2 |
| 37 | Product of Example 2 | 1 month | 3 | 13 | 32 | 53 | 24.9 |
| 38 | Product of Example 2 | 2 months | 17 | 13 | 32 | 55 | 25.2 |

| Example | Additive | Storage time at 50° C. | Viscosity % increase | Foam parameters | | | OI % |
|---|---|---|---|---|---|---|---|
| | | | | CT (sec) | RT (sec) | NTT (sec) | |
| | DMMP | 0 | 0 | 21 | 65 | 130 | 25.4 |
| | DMMP | 1 month | 700 | Unacceptable quality foam | | | |
| | DMMP | 2 months | 1747 | | | | |

We claim:
1. A flame retardant composition comprising
(a) a polyurethane or a polyisocyanurate, and
(b) an effective amount of a salt formed by the reaction of one to two molar equivalents of dimethyl methylphosphonate, monomethyl methylphosphonate or methylphosphonic acid with one molar equivalent of a compound of formula I

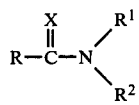

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms, or R is a group

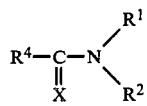

where $R^1$, $R^2$ and X are as defined above and $R^4$ is a direct bond or $R^4$ is alkylene having 1 to 8 carbon atoms or arylene having 6 to 10 carbon atoms.

2. A composition according to claim 1 in which the salt of component (b) is prepared from a compound of formula I where R is $NHR^3$ where $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms.

3. A composition according to claim 1 in which the salt of component (b) is prepared from a compound of formula I in which R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, and $R^1$ and $R^2$ are the same or different and are H or alkyl with 1 to 4 carbon atoms.

4. A composition according to claim 1 in which the salt of component (b) is prepared from a compound of formula I in which R is a group

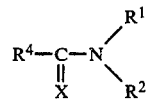

wherein X is O, S or NH, $R^1$ and $R^2$ are the same or different and are H or alkyl with 1 to 4 carbon atoms, and $R^4$ is a direct bond or $R^4$ is alkylene having up to 8 carbon atoms or arylene having 6 to 10 carbon atoms.

5. A composition according to claim 1 in which the salt of component (b) is prepared from a compound of formula I where R and $R^1$ together form an alkylene chain of 3 to 10 carbon atoms.

6. A composition according to claim 1 in which the salt of component (b) is prepared from a compound of formula I which is urea.

7. A mixture which is a flame retardant and which comprises
(a) 5 to 95 percent by weight of a salt formed by the reaction of one to two molar equivalents of dimethyl methylphosphonate, monomethyl methylphosphonate or methylphosphonic acid with one molar equivalent of a compound of formula I

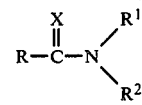

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms, or R is a group

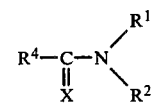

wherein $R^1$, $R^2$ and X are as defined above and $R^4$ is a direct bond or $R^4$ is alkylene having 1 to 8 carbon atoms or arylene having 6 to 10 carbon atoms, and
(b) 95 to 5 percent by weight of a second flame retardant compound selected from the group consisting of the aliphatic and aromatic bromine compounds, oxyalkylated phosphate esters, chloroalkyl phosphates, chloroalkyl phosphonates and triaryl phosphates.

8. A mixture which is a flame retardant and which comprises
(a) 5 to 95 percent by weight of a salt formed by the reaction of one to two molar equivalents of dimethyl methylphosphonate, monomethyl methylphosphonate or methylphosphonic acid with one molar equivalent of a compound of formula I

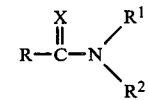

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, CONH₂ or NH₂ or R³ together with R¹ forms an alkylene chain of 2 or 3 carbon atoms, or R is a group

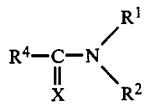

where R¹, R² and X are as defined above and R⁴ is a direct bond or R⁴ is alkylene having 1 to 8 carbon atoms or arylene having 6 to 10 carbon atoms, and (b) 95 to 5 percent by weight of one or more amine salt of a phosphonic acid having the formula VI or VII

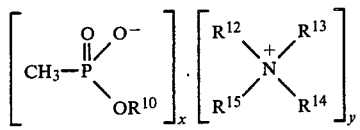   VI

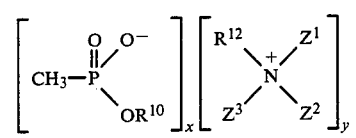   VII wherein x and y are integers such that the number of negative and positive charges are the same, wherein R¹⁰ and R¹² are hydrogen or methyl, R¹³ is a C₂-C₄ alkyl group substituted by 1-3 hydroxyl groups, which may be substituted by an oxyalkylene chain, these being not more than one hydroxyl group on any one carbon atom, R¹⁴ and R¹⁵ may be the same or different and may be a group as defined for R¹³, or hydrogen, a C₁-C₄ alkyl group, a phenyl group, a benzyl group, or a phenyl or benzyl group substituted on the aromatic ring by an alkyl group of 1-12 carbon atoms, a hydroxyl group, which may be substituted by an oxyalkylene chain, and/or 1-3 halogen atoms, or R¹⁵ is a group of the formula (VIII)

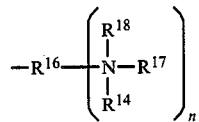   VIII wherein R¹⁶ is an alkylene group of 2-4 carbon atoms, a phenylene group, a xylylene group, a diphenyl methane group or is a group of the formula

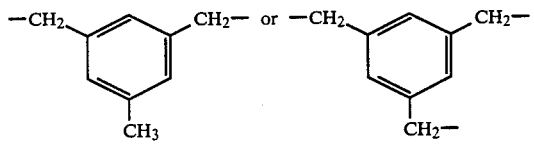

in which aromatic rings in a group R¹⁶ may be substituted by an alkyl group of 1-12 carbon atoms, a hydroxyl group, which may be substituted by an oxyalkylene chain, and/or 1-3 halogen atoms, and R¹⁷ is hydrogen or methyl, in which cases the nitrogen atom carries a positive charge, or R¹⁷ is absent, R¹⁸ is hydrogen or a group as defined for R¹³ and n is 1 or 2;

or R¹⁴ and R¹⁵ may be joined to form, with the nitrogen, 5 or 6 membered heterocyclic ring, optionally containing an oxygen atom; and Z¹, Z² and Z³ are the same or different and represent hydrogen, a C₁-C₁₂ straight or branched chain alkyl group, a C₃-C₁₂ straight or branched chain alkynyl group, a C₄-C₁₂ cycloalkyl group, a phenyl or naphthyl group which may be substituted by a C₁-C₄ straight or branched chain alkyl group, a C₁-C₄ alkoxy group, amino, methylamino, halogen or nitro, or a C₇-C₁₂ aralkyl group.

9. A storage-stable composition, which is capable of reacting with a polyisocyanate to form a polyurethane, which comprises (a) a polyol, and (b) 1 to 100 parts by weight, per 100 parts by weight of polyol of component (a), of a salt formed by the reaction of one to two molar equivalents of dimethyl methylphosphonate, monomethyl methylphosphonate or methylphosphonic acid with one molar equivalent of a compound of formula I

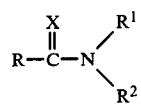   I in which X is O, S or NH, R¹ is H, alkyl with 1 to 4 carbon atoms, alkenyl with 2 to 4 carbon atoms, CN, CONH₂ or NH₂, R² is H, alkyl with 1 to 4 carbon atoms or alkenyl with 2 to 4 carbon atoms or R¹ and R² together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with R¹ forms an alkylene chain of 3 to 10 carbon atoms, or R is a group NHR³ wherein R³ is H, alkyl with 1 to 4 carbon atoms, alkenyl with 2 to 4 carbon atoms, CN, CONH₂ or NH₂ or R³ together with R¹ forms an alkylene chain of 2 or 3 carbon atoms, or R is a group

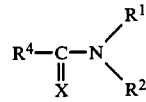

where R¹, R² and X are as defined above and R⁴ is a direct bond or R⁴ is alkylene having 1 to 8 carbon atoms or arylene having 6 to 10 carbon atoms; or of a composition containing preformed polyurethane or polyisocyanurate and an effective amount of the salt defined above.

10. A composition according to claim 9 which contains 3 to 50 parts by weight of component (b) per 100 parts by weight of polyol of component (a).

11. A process for preparing a flame retardant polyurethane or polyisocyanurate which comprises reacting a polyol with a stoichiometric amount of a polyisocyanate in the presence of a salt formed by the reaction of one to two molar equivalents of dimethyl methylphosphonate, monomethyl methylphosphonate or methylphosphonic acid with one molar equivalent of a compound of formula I $$R-\overset{X}{\underset{\|}{C}}-N\overset{R^1}{\underset{R^2}{\diagdown}} \quad \text{I}$$

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms, or R is a group $$R^4-\underset{\underset{X}{\|}}{C}-N\overset{R^1}{\underset{R^2}{\diagdown}}$$

where $R^1$, $R^2$ and X are as defined above and $R^4$ is a direct bond or $R^4$ is alkylene having 1 to 8 carbon atoms or arylene having 6 to 10 carbon atoms; wherein the amount of said salt is 1 to 100 parts by weight per 100 parts by weight of polyol.

12. A process according to claim 11 wherein an effective amount of a blowing agent is also present.

13. A process according to claim 11 wherein the amount of said salt or said composition is 3 to 50 parts by weight per 100 parts by weight of polyol.

14. A salt formed by the reaction of one to two molar equivalents of dimethyl methylphosphonate, monomethyl methylphosphonate or methylphosphonic acid with one molar equivalent of a compound of formula I $$R-\overset{X}{\underset{\|}{C}}-N\overset{R^1}{\underset{R^2}{\diagdown}} \quad \text{I}$$

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms, or R is a group $$R^4-\underset{\underset{X}{\|}}{C}-N\overset{R^1}{\underset{R^2}{\diagdown}}$$

where $R^1$, $R^2$ and X are as defined above and $R^4$ is a direct bond or $R^4$ is alkylene having 1 to 8 carbon atoms or arylene having 6 to 10 carbon atoms, with the proviso that the salt is not one formed by the reaction of methylphosphonic acid and dicyandiamide or of methylphosphonic acid and guanidine.

15. A salt according to claim 14 in which the compound of formula I is urea.

16. A process for preparing a salt formed by the reaction of one to two molar equivalents of dimethyl methylphosphonate, monomethyl methylphosphonate or methylphosphonic acid with one molar equivalent of a compound of formula I $$R-\overset{X}{\underset{\|}{C}}-N\overset{R^1}{\underset{R^2}{\diagdown}} \quad \text{I}$$

in which X is O, S or NH, $R^1$ is H, alkyl with 1 to 4 carbon atoms, alkenyl with 2 to 4 carbon atoms, CN, $CONH_2$ or $NH_2$, $R^2$ is H, alkyl with 1 to 4 carbon atoms or alkenyl with 2 to 4 carbon atoms or $R^1$ and $R^2$ together with the nitrogen atom to which they are attached form a pyridine, morpholine, piperidine or piperazine ring, and R is H, alkyl with 1 to 8 carbon atoms, aryl with 6 to 10 carbon atoms, cycloalkyl with 5 to 12 carbon atoms, pyridyl, morpholyl, piperidyl, indolyl or quinolyl, or R together with $R^1$ forms an alkylene chain of 3 to 10 carbon atoms, or R is a group $NHR^3$ wherein $R^3$ is H, alkyl with 1 to 4 carbon atoms, alkenyl with 2 to 4 carbon atoms, CN, $CONH_2$ or $NH_2$ or $R^3$ together with $R^1$ forms an alkylene chain of 2 or 3 carbon atoms, or R is a group $$R^4-\underset{\underset{X}{\|}}{C}-N\overset{R^1}{\underset{R^2}{\diagdown}}$$

where $R^1$, $R^2$ and X are as defined above and $R^4$ is a direct bond or $R^4$ is alkylene having 1 to 8 carbon atoms or arylene having 6 to 10 carbon atoms, which comprises mixing dimethyl methylphosphonate, monomethyl methylphosphonate or methylphosphonic acid with a compound of formula I with the proviso that the salt is not one formed by the reaction of methylphosphonic acid and dicyandiamide or of methylphosphonic acid and guanidine at room temperature or at temperatures up to 180° C.

17. A process according to claim 16 in which an aqueous or organic solvent is used.

18. A process according to claim 16 in which an inert gas atmosphere is used.

19. A process according to claim 16 in which dimethyl methylphosphonate is used and the reaction is effected by heating at temperatures up to 180° C. under an inert gas atmosphere.

* * * * *